(12) United States Patent
Spivack et al.

(10) Patent No.: US 6,414,200 B1
(45) Date of Patent: Jul. 2, 2002

(54) SILYLMETHANETHIOLS AS PROMOTERS FOR BISPHENOL PRODUCTION

(75) Inventors: James Lawrence Spivack, Cobleskill; Jimmy Lynn Webb, Ballston Lake; Victoria Jean Eddy-Helenek, Scotia; Joseph Richard Wetzel, Watervliet, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/741,627

(22) Filed: Dec. 19, 2000

(51) Int. Cl.$^7$ ................................................. C07L 39/16
(52) U.S. Cl. ........................ 568/728; 502/158; 568/727
(58) Field of Search .................................. 568/727, 728

(56) References Cited

FOREIGN PATENT DOCUMENTS

EP            771589 A1     5/1997

*Primary Examiner*—Michael L. Shippen
(74) *Attorney, Agent, or Firm*—Andrew J. Caruso; Noreen C. Johnson

(57) ABSTRACT

Silylmethanethiols have been found to be useful promoters in the acid catalyzed condensation reaction between phenol and acetone to afford bisphenol A. Silylmethanethiols provide improvements in both the rate and selectivity of bisphenol A formation relative to known thiol promoters such as 3-mercaptopropionic acid or hexanethiol.

19 Claims, No Drawings

SILYLMETHANETHIOLS AS PROMOTERS FOR BISPHENOL PRODUCTION

BACKGROUND OF THE INVENTION

This invention relates to silylmethanethiols and their use as promoters in the reaction of hydroxyaromatic compounds with aldehydes and ketones in the presence of an acidic catalyst to afford bisphenols, such as bisphenol A (BPA).

Bisphenols, as exemplified by BPA, are widely employed in the manufacture of polymeric materials and are typically prepared by condensation of a hydroxyaromatic compound with an aldehyde or ketone in the presence of an acidic catalyst. Bisphenol A (BPA) is the principal monomer used in the manufacture of bisphenol A polycarbonate, a commercial engineering thermoplastic material. The manufacture of bisphenol A (BPA) from acetone and phenol is practiced globally on a large scale with hundreds of millions of pounds of BPA produced annually. Typically, phenol is reacted with acetone in the presence of an acidic catalyst and a thiol promoter. The thiol promoter acts to improve the rate and selectivity of BPA formation in the acid catalyzed condensation of phenol with acetone. Many different combinations of acidic catalysts and thiol promoters have been investigated and some thiol promoters such as 3-mercaptopropionic acid have been employed in the commercial scale production of BPA. Notwithstanding earlier research efforts and their attendant impressive process improvements in the manufacture of bisphenols such as bisphenol A, there is a continuing need to improve further both the rate and selectivity of bisphenol formation in the acid catalyzed condensation of hydroxyaromatic compounds with aldehydes or ketones.

BRIEF SUMMARY OF THE INVENTION

In one aspect the present invention relates to A method for making a bisphenol, said method comprising contacting a mixture comprising a hydroxyaromatic compound and a ketone or an aldehyde with an acidic catalyst at a temperature in a range between about 25° C. and about 95° C. in the presence of a silylmethanethiol promoter having structure I:

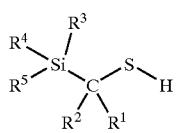

I wherein
$R^1$ and $R^2$ are each independently hydrogen, a $C_1$–$C_{40}$ aliphatic radical, a $C_3$–$C_{40}$ aromatic radical, a $C_3$–$C_{40}$ cycloaliphatic radical, or
$R^1$ and $R^2$ together form a $C_3$–$C_{40}$ cycloaliphatic radical or a $C_4$–$C_{40}$ aromatic radical;
$R^3$–$R^5$ are each independently a $C_1$–$C_{40}$ aliphatic radical, a $C_3$–$C_{40}$ aromatic radical, or a $C_3$–$C_{40}$ cycloaliphatic radical; or
any two of the groups $R^3$–$R^5$ together form a $C_5$–$C_{40}$ cycloaliphatic radical or $C_5$–$C_{40}$ aromatic radical; or
the groups $R^3$–$R^5$ together form a $C_9$–$C_{40}$ cycloaliphatic radical or $C_{10}$–$C_{40}$ aromatic radical.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

The term "thiol promoter" as used herein refers to a molecule incorporating a thiol (SH) group. The thiol promoter acts to improve either one of, or both, the rate and selectivity of bisphenol formation when a hydroxyaromatic compound is condensed with an aldehyde or ketone in the presence of an acidic catalyst relative to the same reaction carried out in the absence of the thiol promoter.

The term "silylmercaptan" as used herein refers to a molecule incorporating a thiol (SH) group and a silicon atom. "BPA" is herein defined as bisphenol A and is also known as 2,2-bis(4-hydroxyphenyl)propane, 4,4'-isopropylidenediphenol and p,p-BPA.

"o,p-BPA" is herein defined as o,p-bisphenol A and is also known as 2-(2-hydroxyphenyl)-2-(4-hydroxyphenyl)propane and 2,4'-isopropylidenediphenol.

As used herein the term "aromatic radical" refers to a radical having a valency of at least one and comprising at least one aromatic group. Examples of aromatic radicals include phenyl, pyridyl, furanyl, thienyl, imidazolyl, naphthyl, phenylene and biphenyl groups. The term includes groups containing both aromatic and aliphatic components, for example a benzyl group. Further, a $C_3$–$C_{40}$ aromatic radical is an aromatic radical comprising between 3 and 40 carbon atoms. The 2-imidazolyl group (i)

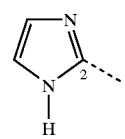

(i)

illustrates a $C_3$ aromatic radical.

As used herein the term "aliphatic radical" refers to a radical having a valency of at least one and comprising a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, and hexamethylene groups.

As used herein the term "cycloaliphatic radical" refers to a radical having a valency of at least one and comprising an array of atoms which is cyclic but which is not aromatic. The array may include heteroatoms such as nitrogen, sulfur and oxygen or may be composed exclusively of carbon and hydrogen. Examples of cycloaliphatic radicals include cyclcopropyl, cyclopentyl cyclohexyl and tetrahydrofuranyl groups.

As used herein the term "carbamyl group" refers to a functional group comprising the array of atoms OCONH. For example a carbamyl group is present the product of reaction of an alcohol with an isocyante as illustrated by the compound 1-naphthyl methylcarbamate, CAS No. 63-25-2.

As used herein the term "Boc group" refers to a an amine protecting group comprising the tertiary-butoxycarbonyl moiety. The combination of a nitrogen atom bearing both a hydrogen atom and the Boc group is an example of a carbamyl group.

The instant invention provides a method of preparing a bisphenol, such as bisphenol A, by acid catalyzed condensation of a hydroxyaromatic compound, such as phenol, with an aldehyde, such as butanal, or ketone, such as acetone, in the presence of a silylmethanethiol promoter having structure I.

In one embodiment of the present invention at least one of the groups R1–R5 contains a basic functional group by which the silylmethanethiol promoter may be attached to a solid catalyst such as a sulfonated polystyrene catalyst by virtue of a strong hydrogen bonding interaction between the silylmethanethiol promoter containing said basic functional group and the catalyst. The silylmethanethiol promoter is thus immobilized on the solid catalyst thereby avoiding the necessity of introduction of the silylmethanethiol promoter with the feed stream, and the eventual recovery of the silylmethanethiol promoter from the product stream. Functional groups which are sufficiently basic to facilitate ionic attachment of the promoter to a polymeric acid catalyst include, but are not limited to amino and pyridyl groups. In some instances the thiol promoter does not contain a functional group which is basic per se, yet the thiol promoter does contain a functional group capable of forming one or more hydrogen bonds with sulfonic acid ($SO_3H$) or sulfonate ($SO_3^-$) groups present in the polymeric acid catalyst, said hydrogen bonds being sufficiently strong to immobilize the thiol promoter on the polymeric acid catalyst. Examples of said functional groups present in the thiol promoter being amido, imido and carbamyl groups as are found in amides, imides and carbamates respectively.

Silylmethanethiols having structure I are known in the chemical

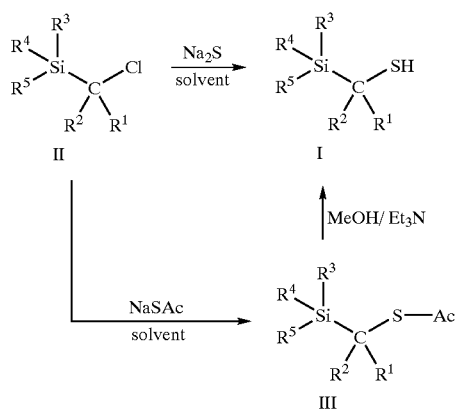

literature and methods for their preparation have been described in, for example, J. Org. Chem. 53(5) 844 (1987); J. Org. Chem. 51(18) 3428 (1986); and Tetrahedron Letters 26 (11) 1425 (1985). In some instances silylmethanethiols having structure I are commercially available as in the case of trimethylsilylmethanethiol which is available from TCI Chemical Company, Portland, Oreg. Other members of this class may be prepared by reaction of a chloromethylsilane having structure II with a sulfur nucleophile such as sodium sulfide, sodium thioacetate or thiourea. Where sodium sulfide is employed the silylmethanthiol I is obtained directly. Where the thioacetate is employed as a nucleophile, acetate derivative III is obtained. The acetate derivative III is readily converted to the corresponding thiol I upon solvolysis, for example upon heating acetate derivative III with methanol in the presence of a basic catalyst such as triethylamine.

Chloromethylsilicon compounds corresponding to structure II may be prepared by a variety of methods, among them the hydrosilylation reaction of olefins having structure IV with a chloromethylsilanes V incorporating a silicone hydride function. Thus, olefin IV in which radical $R^6$ corresponds to a two carbon lower homolog of radical $R^5$ may be reacted with chloromethylsilane V in the presence of a noble metal catalyst to afford chloromethylsilicon derivative II.

A variety of reaction conditions may be employed for the conversion

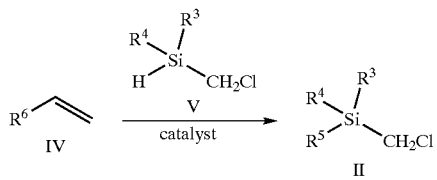

of chloromethylsilanes II into silylmethanethiols I and silylmethanethiol acetate derivatives III. Typically, the chloromethylsilane is combined in a polar solvent such as methanol or dimethylformamide with a slight excess of sodium sulfide or sodium thioacetate and the mixture us stirred at a temperature between about 0° C. and about 100° C. until all of the starting chloromethylsilane has been consumed as judged by gas chromatography, thin layer chromatography or like analytical technique. Thereupon, the reaction mixture may be distributed between water and a solvent such as toluene or ethyl acetate. The organic layer is then washed with water to complete the removal of inorganic salts and then dried over a suitable drying agent such as magnesium sulfate. Filtration and solvent evaporation affords the crude product which may be employed as a promoter for BPA production in its crude state, or purified, for example by column chromatography or recrystallization, prior to such use.

Examples of silylmethanethiols which may be used as promoters for bisphenol production include, but are not limited to, trimethylsilylmethanethiol, triethylsilylmethanethiol, tripropylsilylmethanethiol, tributylsilylmethanethiol, 1-trimethylsilyl-1-ethylmethanethiol and 1-trimethylsilyl-1-benzylmethanethiol. Where the silylmethanethiol is to be used as a bulk promoter, that is a promoter which is not adapted for attachment to a solid acid catalyst via a strong hydrogen bonding interaction or other covalent bond, the preferred silylmethanethiol promoter is trimethylsilylmethanethiol owing to its availability, ease of preparation and recovery or removal from the reaction product.

In some instances it may be advantageous to employ a silylmethanethiol derivative such as trimethylsilylmethanethiol acetate in the process of the present invention. Under such circumstances it is believed that the silylmethanethiol acetate is converted to the active silylmethanethiol promoter under the reaction conditions. Silylmethanethiol acetates and other silylmethanethiol derivatives which afford a silylmethanethiol under the reaction conditions are advantageously employed at about the same levels as the silylmethanethiol itself.

In some instances the silylmethanethiol promoter may function as an attached promoter, as is the case of those silylmethanethiols which incorporate an amine function which may be used to form an attachment to a solid phase catalyst such as a sulfonated polystyrene. The attachment of the silylmethanethiol to the solid phase catalyst may be based upon a strong hydrogen bonding interaction or a covalent bond. Examples of silylmethanethiols which may be used as attached promoters for bisphenol production include: 3-aminopropyldimethylsilylmethanethiol, 3-N-methylaminopropyldimethylsilylmethanethiol, 3-N,N-dimethylaminopropyldimethylsilylmethanethiol, 3-(1-piperadinyl)propyldimethylsilylmethanethiol, and 2-(4-pyridyl)ethyldimethylsilylmethanethiol.

In addition to silylmethanethiols which incorporate a free amino function, derivatives of such materials incorporating acylated thiol groups and protected amine groups may also be employed. Thus, the N-Boc-3-aminopropyldimethylsilylmethanethiol acetate derivative VI is found to function as an effective attached promoter for bisphenol production. Thiol acetate VI is believed to be converted to 3-aminopropyldimethyl-silylmethanethiol VII under the conditions

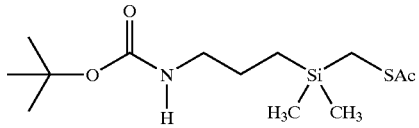

VI used to prepare bisphenols.

As noted, the instant invention provides a method of preparing a

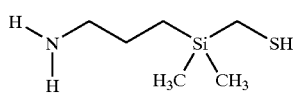

VII bisphenol by acid catalyzed condensation of a hydroxyaromatic compound with an aldehyde or ketone in the presence of a silylmethanethiol promoter having structure I. Examples of hydroxyaromatic compounds include phenol, o-cresol, m-cresol, 2-t-butylphenol, 2-propylphenol and 1-naphthol. Examples of aldehydes include formaldehyde, acetaldehyde, propionaldehyde and butanal. Examples of ketones include acetone, cyclohexanone; 3,3,5-trimethylcyclohexanone and 2-butanone.

A wide variety of bisphenols; such as 2,2-bis(4-hydroxyphenyl)propane; 2,2-bis(4-hydroxy-3-methylphenyl)propane; 1,1-bis(4-hydroxyphenyl)cyclohexane; 1,1-bis(4-hydroxy-3-methylphenyl)cyclohexane and 1,1-bis(4-hydroxyphenyl)-3,3,5-trimethylcyclohexane, may be prepared by the method of the present invention. The present invention is best exemplified by its use in the preparation of bisphenol A via condensation reaction of phenol with acetone. A mixture comprising phenol and acetone is contacted with an acidic catalyst and silylmethanethiol promoter at a temperature between about 20° C. and about 100° C., preferably between about 40° C. and about 90° C. and still more preferably between about 50° C. and about 80° C.

Typically, the acidic catalyst will be a either a sulfonated polystyrene derivative comprising structural units VIII or a non-polymeric mineral acid or an organic sulfonic acid or a fluorinated carboxylic acid. Polymeric acidic resins comprising structure IV are exemplified by Amberlyst® 131, Amberlyst® 15 and Amberlyst® 36, all of which are strongly acidic ion exchange resins available from the Rohm and Haas Company.

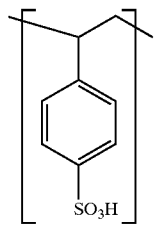

VIII

Other suitable polymeric acidic catalysts which may be used in the preparation of bisphenol A include Nafion® perfluorinated acidic resins available from the Dupont Company. In some instances it may desirable to employ a non-polymeric acid as the catalyst. Examples of suitable non-polymeric acid catalysts include HCl, HBr, HI, $BF_3$, HF, $MeSO_3H$ and $CF_3CO_2H$.

Where the catalyst employed is a polymer supported acidic catalyst the reactants, phenol, acetone and silylmethanethiol promoter may be passed through a catalyst bed in a continuous fashion. Alternatively, a catalyst may be pretreated with the silylmethanethiol promoter comprising a functional group capable of a strong hydrogen bonding interaction with the acidic catalyst. In the case of a silylmethanethiol attached to a solid acidic catalyst by a strong hydrogen bonding interaction, the preferred loading of said silylmethanethiol on the solid acid catalyst is in a range corresponding to between about 10 and about 60 percent of the acid sites present in the solid catalyst. For a sulfonated polystyrene originally comprising about 5 milliequivalents of $SO_3H$ groups per gram of resin, between about 10 and 60 percent of the acid sites corresponds to a loading of silylmethanethiol of between about 0.5 and about 3.0 milliequivalents per gram of resin.

Typically the feed is introduced at a weight hourly space velocity of from about 0.1 to about 6, preferably from about 0.3 to about 3, and even more preferably from about 0.2 to about 1.6 pounds of the feed mixture per pound catalyst per hour. The feed mixture comprises from about 0.1 to about 10 weight percent acetone and about 70 to about 99 weight percent phenol, preferably about 3 to about 8 weight percent acetone and about 85 to about 96 weight percent phenol, and still more preferably about 3 to about 6 weight percent acetone and about 90 to about 96 weight percent phenol. The amount of silylmethanethiol promoter is preferably in a range between about 5 and about 100 millimoles per liter (mmol/L) of feed, preferably about 10 to about 75 mmol/L and even more preferably about 20 to about 40 mmol/L of feed.

The reaction may be also conducted using a soluble acidic catalyst such as methanesulfonic acid. The reaction may be carried out as a batch or continuous process. The reactants are charged to a stirred reactor adapted as desired for batch or continuous operation. Typically a feed solution containing phenol, acetone and promoter are introduced and the acidic catalyst is added separately. The amount of acidic catalyst employed is such that the reaction mixture contains from about 10 to about 1000 mmol of acidic catalyst per liter, preferably from about 20 to about 500 mmol of acidic catalyst per liter, and still more preferably from about 100 to about 300 mmol of acidic catalyst per liter. The reaction mixture comprises from about 0.1 to about 10 weight percent acetone and about 70 to about 99 weight percent phenol, preferably about 3 to about 8 weight percent acetone and about 85 to about 96 weight percent phenol, and still more preferably about 3 to about 6 weight percent acetone and about 90 to about 96 weight percent phenol. The amount of silylmethanethiol promoter is preferably in a range between about 5 and about 100 millimoles per liter (mmol/L) of reaction mixture, preferably about 10 to about 75 mmol/L and even more preferably about 20 to about 40 mmol/L.

EXAMPLES

The following examples are put forth so as to provide those of ordinary skill in the art with a detailed disclosure and description of how the methods claimed herein are evaluated. Unless indicated otherwise, parts are by weight, temperature is in degrees centigrade. The materials and testing procedures used for the results shown herein are as follows:

Starting material and product compositions were determined by gas chromatography on a Hewlett Packard model 5890 chromatograph. GC-mass spectral data were obtained on a Hewlett Packard model 5971A GC-MS. The laboratory robot employed was an 8-probe Gilson 215 modified to be able to transfer molten phenolic solutions.

The surprising effect of silylmethanethiol promoter was demonstrated on a laboratory scale in a reaction vessel designed to act as a stirred tank reactor operated in a continuous mode. Sampling was carried out under steady state conditions. Thus, a septum-sealed 96 well polypropylene block, equipped with miniature magnetic spin bars, was charged with one or more stock solutions containing reactants, promoter and optionally an acidic catalyst, by means of a laboratory robot. The reaction was stirred and heated for a period of 5.4 minutes at which time a portion of the reaction mixture (37 percent by volume) was removed. After an additional 5.4 minutes additional reactants, promoter and optionally an acidic catalyst were added in an amount just sufficient to replace the amount removed. This mixture was then stirred and heated for a period of 5.4 minutes at which point the cycle was repeated. The periodic removal of a portion of the reaction mixture and the reintroduction of additional of fresh reactants, thiol promoter and optionally an acidic catalyst were carried out using the laboratory robot. After twenty such cycles the reaction mixture was considered to have achieved a steady state and the reaction mixture was analyzed. The reaction block was heated by means of a heating block and the reaction temperature was 70° C.+/−1° C.

Example 1 and Comparative Examples No. 1 and 2

A liquid handling robot was used to sequentially deliver equal volumes of two molten phenolic stock solutions to stirred reactors maintained at 70° C. The first stock solution contained 10.6% by weight acetone and was 61.6 millimolar (mM) in promoter in molt en phenol. The second contained 565 mM methanesulfonic acid in phenol. When all reactors had been charged with both stock solutions, an aliquot was removed from each reactor so that the total volume in the reactor was constant from cycle to cycle. This constituted one cycle. At the end of cycle 20 the aliquot removed was divided into two samples each of which were analyzed. The delivery volume of each stock solution was about 18.8% of the minimum standing volume in the reactor and the cycle time was about 10.75 minutes. Thus 37% of the reactor volume was exchanged every 10.75 minutes and liquid residence time is about 30 minutes. The liquid handling robot introduced some solvent (phenol) dilution in every transfer which resulted in a dilution in a range from about 8 to about 13%. Also, the two stock solutions w ere mixed in equal amounts in the reactors. Thus actual pre-reaction concentrations in the reactors were: acetone 4.7–4.9%, promoter 27.3–28.5 mM and methanesulfonic acid 250–262 mM. Results are provided in Table I and illustrate the superiority of the silylmethanethiol promoter relative to a known promoter, 3-mercaptopropionic acid (Comparative Example No. 1). Comparative Example No. 2 was run without added promoter. Values given in Table I are average values based on 4 or more replicates.

TABLE I

| Example | Promoter Structure | Selectivity pp/op[b] | Selectivity % p,p-BPA[c] | wt % BPA[d] |
|---|---|---|---|---|
| Example 1 | Si-CH₂-SH | 27.42 | 94.57 | 10.6 |
| CE-1[a] | HS-CH₂-CH₂-C(=O)-O-H | 20.06 | 93.89 | 7.0 |
| CE-2 | None present | 5.09 | 81.55 | 2.1 |

[a]Comparative Example
[b]Selectivity = weight percent p,p-BPA present in the reaction mixture divided by the weight percent o,p-BPA present in the reaction mixture
[c]Selectivity expressed as weight % p,p-BPA in product mixture relative to all other phenol/acetone condensation products present in the reaction mixture
[d]Weight percent p,p-BPA in product mixture at cycle 20. Concentration is not corrected for a robotic dilution of about 10%

Example 2 and Comparative Examples No. 3–6

A robotic liquid handling system as in Example 1 was used to deliver a stock solution containing phenol, acetone and promoter to stirred reactors maintained at 70° C. containing from about 47 to about 49 milligrams of 4% crosslinked sulfonated polystyrene. The reactors themselves were part of an eight probe incremental flow reactor. The concentrations of reagents in the stock solution delivered to the reactors were as follows: acetone, about 8 weight percent, promoter 54.5 mmol/L and phenol about 91 weight percent. Each stirred reactor was fed the stock solution which was stirred for 7 minutes at 70° C. after which time a portion of the reaction mixture was removed. After an additional 7 minutes additional stock solution was added in an amount equal to the volume previously removed from the reactor. This "making up" of the volume of the reaction mixture completed a "cycle". Liquid residence time was about 1 hour and the throughput of stock solution was about 3 grams of stock solution per gram resin catalyst per hour. The reactors were run in this manner for 40 cycles and then sampled and analyzed by gas chromatography. Each reaction was replicated at least 4 times. Results are given in Table II.

TABLE II

| Examples | Promoter Structure | Selectivity pp/op[b] | Selectivity % p,p-BPA[c] | wt % BPA[d] |
|---|---|---|---|---|
| Example 2 | Si-CH₂-SH | 24.26 | 93.67 | 16.89 |
| CE[a]-3 | HS-CH₂-CH₂-C(=O)-O-H | 20.21 | 93.25 | 15.16 |
| CE-4 | HS-(CH₂)₄-CH₃ | 18.83 | 92.86 | |

TABLE II-continued

| Examples | Promoter Structure | Selectivity pp/op[b] | Selectivity % p,p-BPA[c] | wt % BPA[d] |
|---|---|---|---|---|
| CE-5 | (Si-CH2CH2-SH structure) | 16.18 | 91.08 | |
| CE-6 | none | 8.34 | 84.79 | |

[a]Comparative Example
[b]Selectivity = weight percent p,p-BPA present in the reaction mixture divided by the weight percent o,p-BPA present in the reaction mixture
[c]Selectivity expressed as weight % p,p-BPA in product mixture relative to all other phenol/acetone condensation products present in the reaction mixture
[d]Weight percent p,p-BPA in product mixture at cycle 20. Concentration is not corrected for a robotic dilution of about 10%.

The data in Table II reveal the superiority of the silyl-methanethiols of the present invention in providing the highest p,p- to o,p-ratio and the highest overall selectivity for p,p-BPA. It is noteworthy that that trimethylsilyl-methanethiol provides improved selectivity relative to known promoters such as 3-mercatopropionic acid (CE-3) and silylmercaptans falling outside of the scope of the present invention (CE-5).

Examples 3–4 and Comparative Examples 8 and 9

A 250 mL 3-necked round bottom flask equipped with reflux condenser, nitrogen inlet, thermometer heating mantle, pressure equalizing addition funnel and magnetic stirrer was charged with 14.36 g (91.3 mmol) of t-butyl N-allylcarbamate and 150 mL of toluene. The olefin and solvent were stirred and heated to about 70° C., then 10 microliters of Karstedt's catalyst (5% Pt solution, about 30 ppm Pt based on olefin) was added. A solution containing 12 g (110.5 mmol) of chloromethyldimethylsilane in 20 mL toluene was added cautiously over about 30 minutes at a rate sufficient to maintain the reaction temperature between about 80 and about 100° C. After addition was completed, the temperature was stirred and heated at about 85° for about 1 hour. GC-MS indicated complete reaction of the olefin to form the silylated compound, N-Boc-3-aminopropylchloromethyldimethylsilane. The solution was transferred to a 500 ml single neck round bottom flask and the solvent and excess silane were stripped via rotary evaporation to yield 25 g of crude product (quantitative yield based on olefin).

Solid potassium thioacetate (1.37 g, 0.012 mol) was charged to a 125 mL reaction bottle equipped with a magnetic stirrer in a nitrogen filled dry box. The bottle was fitted with a septum and removed from the dry box. Methanol (30 mL) was added and the mixture was stirred to dissolve the potassium thiol acetate. Crude N-Boc-3-aminopropylchloromethyldimethylsilane (2.65 g, 0.01 mol) was then added via syringe and the mixture was warmed to about 50° for about 4.5 hr. Thereafter the mixture was allowed to stand at room temperature for about 48 hr. Water (50 mL) and methylene chloride (50 mL) were added and the phases separated. The organic layer was washed twice with water, dried over sodium sulfate, filtered through a column of silica gel and concentrated under reduced pressure to afford the N-Boc-3-aminopropyldimethylsilylmethanethiol acetate derivative VI (2.84 g) as a nearly colorless oil the $^1$H-NMR, $^{13}$C-NMR and GC-MS of which were fully consistent with structure VI.

A sulfonated polystyrene resin (Amberlyst 131®, 45 milligrams) having approximately 5 milliequivalents per gram $SO_3H$ groups, was charged to multiple wells of a 96 well septum sealed polypropylene block, each well of which served as a reaction vessel and was equipped for magnetic stirring. Phenol (180 microliters) was added to each well containing the resin and the mixture was stirred and heated at 70° for 1 hr. A solution of compound VI in phenol (100 microliters) having a concentration of 450 millimole VI per liter was then added to each of the reactor wells and the mixture was stirred for 2 hr. A series of identically treated reactor wells was prepared using Amberlyst 131® treated with N-Boc-aminoethanthiol served as controls (See Comparative Examples 7 and 8). Thus, each of the reaction vessels containing resin and either promoter VI or N-Boc-aminoethanthiol contained about 1 millimole of promoter per gram of resin. A stock solution containing 91% by weight phenol and 9% by weight acetone was added to, and removed from, each of the reactor wells as described in Example 2. After 40 cycles, each of the reaction wells were sampled and analyzed. Data are provided in Table III which demonstrate the marked superiority of compound VI (Examples 3–4) relative to N-Boc-aminoethanthiol (Comparative Examples 7 and 8).

TABLE III

| Examples | Promoter Structure | Selectivity pp/op[d] | Selectivity % p,p-BPA[e] | wt % BPA[f] |
|---|---|---|---|---|
| Example 3 | VI[b] | 42.68 | 95.27 | 28.60 |
| Example 4 | VI | 43.49 | 95.27 | 28.12 |
| CE[a]-7 | N-Boc-cysteamine[c] | 22.19 | 93.71 | 19.29 |
| CE-8 | N-Boc-cysteamine | 22.03 | 93.70 | 19.71 |

[a]Comparative Example
[b]VI = N-Boc-3-aminopropyldimethylsilylmethanethiol acetate
[c]2-N-Boc-ethanethiol
[d]Selectivity = weight percent p,p-BPA present in the reaction mixture divided by the weight percent o,p-BPA present in the reaction mixture
[e]Selectivity expressed as weight % p,p-BPA in product mixture relative to all other phenol/acetone condensation products present in the reaction mixture
[f]Weight percent p,p-BPA in product mixture at cycle 20.

The invention has been described in detail with particular reference to preferred embodiments thereof, but it will be understood that variations and modifications can be effected within the spirit and scope of the invention.

What is claimed is:

1. A method for making a bisphenol, said method comprising contacting a mixture comprising a hydroxyaromatic compound and a ketone or an aldehyde with an acidic catalyst at a temperature in a range between about 25° C. and about 95° C. in the presence of a silylmethanethiol promoter having structure I, wherein $R^1$ and $R^2$ are each independently hydrogen, a $C_1$–$C_{40}$ aliphatic radical, a $C_3$–$C_{40}$

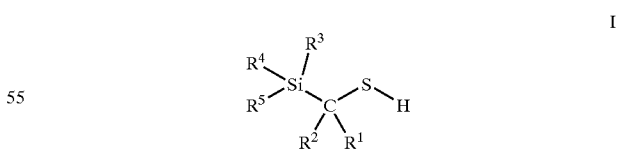

I aromatic radical, a $C_3$–$C_{40}$ cycloaliphatic radical, or
$R^1$ and $R^2$ together form a $C_3$–$C_{40}$ cycloaliphatic radical or a $C_4$–$C_{40}$ aromatic radical;
$R^3$–$R^1$ are each independently a $C_1$–$C_{40}$ aliphatic radical, a $C_3$–$C_{40}$ aromatic radical, or a $C_3$–$C_{40}$ cycloaliphatic radical; or
any two of the groups $R^3$–$R^1$ together form a $C_5$–$C_{40}$ cycloaliphatic radical or $C_5$–$C_{40}$ aromatic radical; or the groups $R^3$–$R^5$ together form a $C_9$–$C_{40}$ cycloaliphatic radical or $C_{10}$–$C_{40}$ aromatic radical.

2. A method according to claim 1 wherein the bisphenol is selected from the group consisting of 2,2-bis(4-hydroxyphenyl)propane; 2,2-bis(4-hydroxy-3-methylphenyl)propane; 1,1-bis(4-hydroxyphenyl)cyclohexane; 1,1-bis(4-hydroxy-3-methylphenyl)cyclohexane and 1,1-bis(4-hydroxyphenyl)-3,3,5-trimethylcyclohexane.

3. A method according to claim 1 wherein said silylmethanethiol is present in an amount in a range between about 5 mmol/L and about 100 mmol/L.

4. A method according to claim 3 wherein said silylmethanethiol is present in an amount in a range between about 10 mmol/L and about 75 mmol/L.

5. A method according to claim 4 wherein said silylmethanethiol is present in an amount in a range between about 20 mmol/L and about 40 mmol/L.

6. A method according to claim 1 wherein said silylmethanethiol is selected from the group consisting of trimethylsilylmethanethiol, triethylsilanemethanethiol, tripropylsilylmethanethiol, tributylsilylmethanethiol, 1-trimethylsilyl-1-ethylmethanethiol and 1-trimethylsilyl-1-benzylmethanethiol.

7. A method according to claim 1 wherein said mixture comprising phenol and acetone contains from about 0.1 to about 10 weight percent acetone and from about 70 to about 99 weight percent phenol.

8. A method according to claim 7 wherein said mixture comprising phenol and acetone contains from about 3 to about 8 weight percent acetone and from about 85 to about 96 weight percent phenol.

9. A method according to claim 8 wherein said mixture comprising phenol and acetone contains from about 4 to about 6 weight percent acetone and from about 90 to about 96 weight percent phenol.

10. A method according to claim 1 wherein the acidic catalyst is a polymeric sulfonic acid incorporating repeat units having structure VIII:

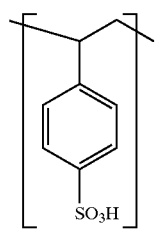

VIII

11. A method according to claim 10 wherein one or more of the groups $R_1$–$R_5$ of silylmethanethiol I incorporates a functional group which forms a strong hydrogen bond with the acidic catalyst.

12. A method according to claim 11 wherein said functional group is selected from the group consisting of amino groups, amido groups, imido groups, and carbamyl groups.

13. A method according to claim 11 wherein the silylmethanethiol promoter has structure VII.

14. A method according to claim 11 wherein the silylmethanethiol is selected from the group consisting of 3-N-methyaminopropyldimethylsilylmethanethiol, 3-N,N-dimethylaminopropyldimethylsilylmethanethiol, 3-(1-piperadinyl)propyldimethylsilylmethanethiol and 2-(4-pyridyl)ethyldimethylsilylmethanethiol.

15. A method according to claim 1 wherein the acidic catalyst is selected from the group consisting of HCl, HBr, HI, HF, $BF_3$, $CH_3SO_3H$ and $CF_3CO_2H$.

16. A method for making bisphenol A, said method comprising condensing phenol with acetone in the presence of an acidic catalyst at a temperature in a range between about 50° C. and about 80° C., said phenol being present in an amount in a range between about 90 and about 95 percent by weight, said acetone being present in an amount in a range between about 4 and about 6 percent by weight, said condensation being carried out in the presence of trimethylsilylmethanethiol promoter, said trimethylsilylmethanethiol promoter being present in an amount between about 10 and about 100 mmol/L of reactants.

17. A method according to claim 16, said acidic catalyst being a sulfonated polystyrene catalyst.

18. A method according to claim 16, said trimethysilylmethanethiol promoter being present in an amount between about 40 and about 40 mmol/L of reactants.

19. A method for making bisphenol A, said method comprising condensing phenol with acetone in the presence of an acidic catalyst at a temperature in a range between about 50° C. and about 80° C., said phenol being present in an amount in a range between about 89 and about 95 percent by weight, said acetone being present in an amount in a range between about 4 and about 10 percent by weight, said catalyst comprising a sulfonated polystyrene comprising sulfonic acid groups and attached aminopropyldimethylsilylmethanethiol promoter having structure VII, said promoter being present in an amount between about 1 mmol per gram of catalyst.

* * * * *